United States Patent
Melvin

(10) Patent No.: US 7,715,918 B2
(45) Date of Patent: May 11, 2010

(54) MUSCLE ENERGY CONVERTER WITH SMOOTH CONTINUOUS TISSUE INTERFACE

(75) Inventor: David Boyd Melvin, Loveland, OH (US)

(73) Assignee: University of Cincinnati, Cincinnati, OH (US)

( * ) Notice: Subject to any disclaimer, the term of this patent is extended or adjusted under 35 U.S.C. 154(b) by 616 days.

(21) Appl. No.: 11/550,653

(22) Filed: Oct. 18, 2006

(65) Prior Publication Data

US 2007/0088402 A1    Apr. 19, 2007

Related U.S. Application Data

(60) Provisional application No. 60/727,650, filed on Oct. 18, 2005.

(51) Int. Cl.
*A61N 1/378* (2006.01)
(52) U.S. Cl. .................................................... 607/35
(58) Field of Classification Search ............. 607/33–35, 607/61
See application file for complete search history.

(56) References Cited

U.S. PATENT DOCUMENTS

| | | | |
|---|---|---|---|
| 2,826,193 A | 3/1958 | Arthur | |
| 3,053,249 A | 9/1962 | Smith | |
| 3,176,316 A | 4/1965 | Bodel | |
| 3,455,298 A | 7/1969 | Anstadt | |
| 3,513,836 A | 5/1970 | Sausse | |
| 3,590,815 A | 7/1971 | Sniff | |
| 3,595,230 A | 7/1971 | Suyeoka et al. | |
| 3,613,672 A | 10/1971 | Schiff | |
| 3,659,615 A * | 5/1972 | Enger | 607/35 |
| 3,668,708 A | 6/1972 | Tindal | |
| 3,713,439 A | 1/1973 | Cabezudo et al. | |
| 3,725,984 A | 4/1973 | Graber | |
| 3,791,388 A | 2/1974 | Rosen et al. | |
| 3,827,426 A | 8/1974 | Page et al. | |
| 3,835,864 A | 9/1974 | Rasor et al. | |
| 3,983,863 A | 10/1976 | Janke et al. | |
| 4,149,277 A | 4/1979 | Bokros | |

(Continued)

OTHER PUBLICATIONS

Geddes et al; Power Capability of Skeletal Muscle to Pump Blood; Trans Am Soc. Artif. Intern Organs. vol. XXXVII; 1991; 6 pages.

(Continued)

*Primary Examiner*—Carl H Layno
*Assistant Examiner*—Hiba El-Kaissi
(74) *Attorney, Agent, or Firm*—Wood, Herron & Evans, L.L.P.

(57) ABSTRACT

A device and corresponding method for converting the contractile work of skeletal muscles into transportable energy. The device may comprise a converter having a mobile end adapted to be connected to a skeletal muscle, a relatively stationary end opposite the mobile end; one or more energy processing units operatively connected to the mobile and stationary ends of the converter, with each energy processing unit adapted to convert tensile forces generated by contraction of the skeletal muscle into transportable energy; and one or more energy conduits such as electrical wires associated with the relatively stationary end of the converter for delivering the transportable energy to power-consuming devices implanted in a body. The device may further comprise a relatively stationary end that is operatively connected to a body structure that is stationary relative to the skeletal muscle.

10 Claims, 10 Drawing Sheets

U.S. PATENT DOCUMENTS

| | | |
|---|---|---|
| 4,187,558 A | 2/1980 | Dahlen et al. |
| 4,192,293 A | 3/1980 | Asrican |
| 4,255,820 A | 3/1981 | Rothermel et al. |
| 4,345,601 A | 8/1982 | Fukuda |
| 4,453,537 A | 6/1984 | Spitzer |
| 4,519,392 A | 5/1985 | Lingua |
| 4,536,893 A | 8/1985 | Parravicini |
| 4,585,458 A | 4/1986 | Kurland |
| 4,597,766 A | 7/1986 | Hilal et al. |
| 4,621,617 A | 11/1986 | Sharma |
| 4,690,134 A | 9/1987 | Snyders |
| 4,713,075 A | 12/1987 | Kurland |
| 4,773,910 A | 9/1988 | Chen et al. |
| 4,809,676 A | 3/1989 | Freeman |
| 4,846,831 A | 7/1989 | Skillin |
| 4,904,255 A | 2/1990 | Chareire et al. |
| 4,917,700 A | 4/1990 | Aikins |
| 4,936,857 A | 6/1990 | Kulik |
| 4,946,377 A | 8/1990 | Kovach |
| 4,957,477 A | 9/1990 | Lundback |
| 4,964,414 A | 10/1990 | Handa et al. |
| 5,013,304 A | 5/1991 | Russell et al. |
| 5,049,155 A | 9/1991 | Bruchman et al. |
| 5,061,283 A | 10/1991 | Silvestrini |
| 5,109,843 A | 5/1992 | Melvin et al. |
| 5,116,372 A | 5/1992 | Laboureau |
| 5,119,804 A | 6/1992 | Anstadt |
| 5,131,905 A | 7/1992 | Grooters |
| 5,139,517 A | 8/1992 | Corral |
| 5,169,381 A | 12/1992 | Snyders |
| 5,192,314 A | 3/1993 | Daskalakis |
| 5,197,983 A | 3/1993 | Berman et al. |
| 5,201,880 A | 4/1993 | Wright et al. |
| 5,217,495 A | 6/1993 | Kaplan et al. |
| 5,256,132 A | 10/1993 | Snyders |
| 5,258,021 A | 11/1993 | Duran |
| 5,334,217 A | 8/1994 | Das |
| 5,345,949 A | 9/1994 | Shlain |
| 5,358,519 A | 10/1994 | Grandjean |
| 5,366,459 A | 11/1994 | Yoon |
| 5,370,685 A | 12/1994 | Stevens |
| 5,383,840 A | 1/1995 | Heilman et al. |
| 5,385,528 A | 1/1995 | Wilk |
| 5,409,499 A | 4/1995 | Yi |
| 5,411,481 A | 5/1995 | Allen et al. |
| 5,417,683 A | 5/1995 | Shiao |
| 5,443,504 A * | 8/1995 | Hill ............................ 623/3.12 |
| 5,456,715 A | 10/1995 | Liotta |
| 5,479,946 A * | 1/1996 | Trumble ..................... 128/899 |
| 5,484,391 A | 1/1996 | Buckman et al. |
| 5,487,760 A | 1/1996 | Villafana |
| 5,533,958 A | 7/1996 | Wilk |
| 5,540,705 A | 7/1996 | Meade et al. |
| 5,571,176 A | 11/1996 | Taheri |
| 5,584,840 A | 12/1996 | Ramsey et al. |
| 5,593,424 A | 1/1997 | Northrup III |
| 5,620,452 A | 4/1997 | Yoon |
| 5,643,308 A | 7/1997 | Markman |
| 5,655,548 A | 8/1997 | Nelson et al. |
| 5,667,526 A | 9/1997 | Levin |
| 5,697,978 A | 12/1997 | Sgro |
| 5,702,343 A | 12/1997 | Alferness |
| 5,709,695 A | 1/1998 | Northrup |
| 5,713,954 A | 2/1998 | Rosenberg et al. |
| 5,738,626 A | 4/1998 | Jarvik |
| 5,738,627 A | 4/1998 | Kovacs et al. |
| 5,749,883 A | 5/1998 | Halpern |
| 5,766,250 A | 6/1998 | Chervitz et al. |
| 5,797,932 A | 8/1998 | Min et al. |
| 5,800,528 A | 9/1998 | Lederman et al. |
| 5,824,071 A | 10/1998 | Nelson et al. |
| 5,846,255 A | 12/1998 | Casey |
| 5,849,019 A | 12/1998 | Yoon |
| 5,910,124 A | 6/1999 | Rubin |
| 5,957,977 A | 9/1999 | Melvin |
| 5,961,440 A | 10/1999 | Schweich et al. |
| 5,981,827 A | 11/1999 | Devlin et al. |
| 6,019,722 A | 2/2000 | Spence et al. |
| 6,045,497 A | 4/2000 | Schweich et al. |
| 6,050,936 A | 4/2000 | Schweich et al. |
| 6,059,715 A | 5/2000 | Schweich et al. |
| 6,077,214 A | 6/2000 | Mortier et al. |
| 6,085,754 A | 7/2000 | Alferness et al. |
| 6,110,100 A | 8/2000 | Talpade |
| 6,123,662 A | 9/2000 | Alferness et al. |
| 6,125,852 A | 10/2000 | Stevens et al. |
| 6,159,224 A | 12/2000 | Yoon |
| 6,162,168 A | 12/2000 | Schweich et al. |
| 6,165,119 A | 12/2000 | Schweich et al. |
| 6,165,120 A | 12/2000 | Schweich et al. |
| 6,165,186 A | 12/2000 | Fogarty et al. |
| 6,170,415 B1 | 1/2001 | Inoue et al. |
| 6,179,791 B1 | 1/2001 | Krueger |
| 6,183,411 B1 | 2/2001 | Mortier et al. |
| 6,214,047 B1 | 4/2001 | Melvin |
| 6,221,103 B1 | 4/2001 | Melvin |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,293,906 B1 | 9/2001 | Vanden Hoek et al. |
| 6,299,621 B1 | 10/2001 | Fogarty et al. |
| 6,312,445 B1 | 11/2001 | Fogarty et al. |
| 6,319,231 B1 | 11/2001 | Andrulitis |
| 6,324,430 B1 | 11/2001 | Zarinetchi et al. |
| 6,324,431 B1 | 11/2001 | Zarinetchi et al. |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,402,680 B2 | 6/2002 | Mortier et al. |
| 6,592,619 B2 | 7/2003 | Melvin |
| 6,945,926 B2 * | 9/2005 | Trumble ..................... 600/16 |
| 7,081,084 B2 | 7/2006 | Melvin |
| 2005/0027332 A1 * | 2/2005 | Avrahami et al. ............. 607/61 |

OTHER PUBLICATIONS

Salmons et al; Cardiac Assistance from Skeletal Muscle: A Critical Appraisal of the Various Approaches; British Heart Journal, vol. 68; 1992; 6 pages.

Reichenbach et al; Characterization and Work Optimization of Skeletal Muscle as a VAD Power Source; ASAIO Journal; 1994; 5 pages.

Farrar et al; A New Skeletal Linear-pull Energy Convertor as a Power Source for Prosthetic Circulatory Support Devices; Journal of Heart and Lung Transplantation; 1992; 9 pages.

Reichenbach et al; In Vivo Studies of an Implantable Energy Convertor for Skeletal Muscle Powered Cardiac Assist; ASAIO Journal, vol. 43; 1997; 5 pages.

Farrar et al; Mechanical Advantage of Skeletal Muscle as a Cardiac Assist Power Source; ASAIO Journal; 1995; 4 pages.

Sasaki et al; A Skeletal Muscle Actuator for an Artificial Heart; ASAIO Journal; 1992; 5 pages.

Acker et al; Skeletal Muscle as the Potential Power Source for a Cardiovascular Pump: Assessment in Vivo; Science, vol. 236; 1987; 4 pages.

Melvin et al; Coupling of Skeletal Muscle to a Prosthesis for Circulatory Support; ASAIO Journal, vol. 43, No. 5; 1997; 8 pages.

Ugolini; Skeletal Muscle for Artificial Heart Drive: Theory and in Vivo Experiments; Biomechanical Cardiac Assist; 1986; 10 pages.

* cited by examiner

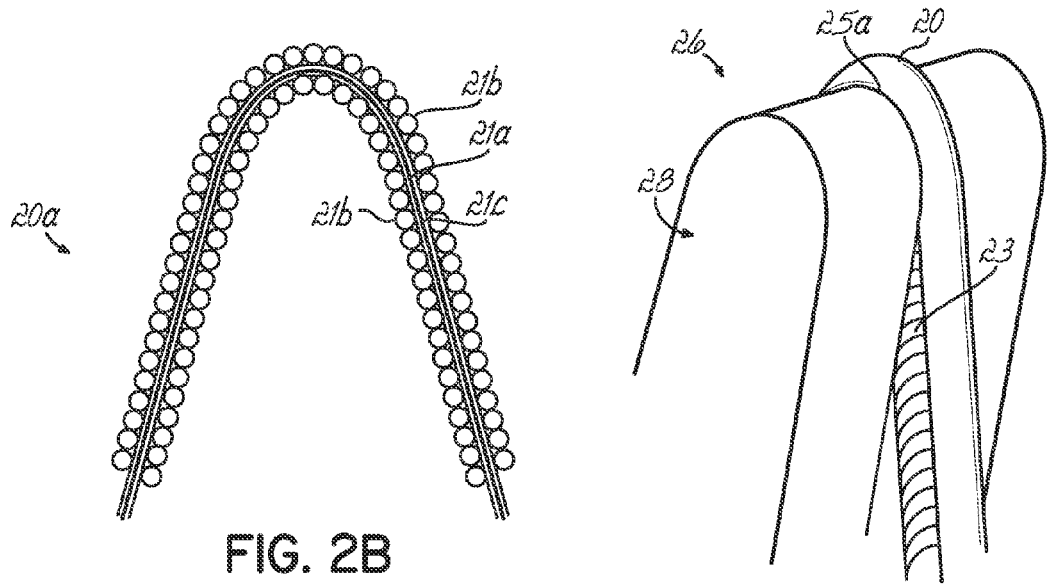
FIG. 2B
FIG. 3
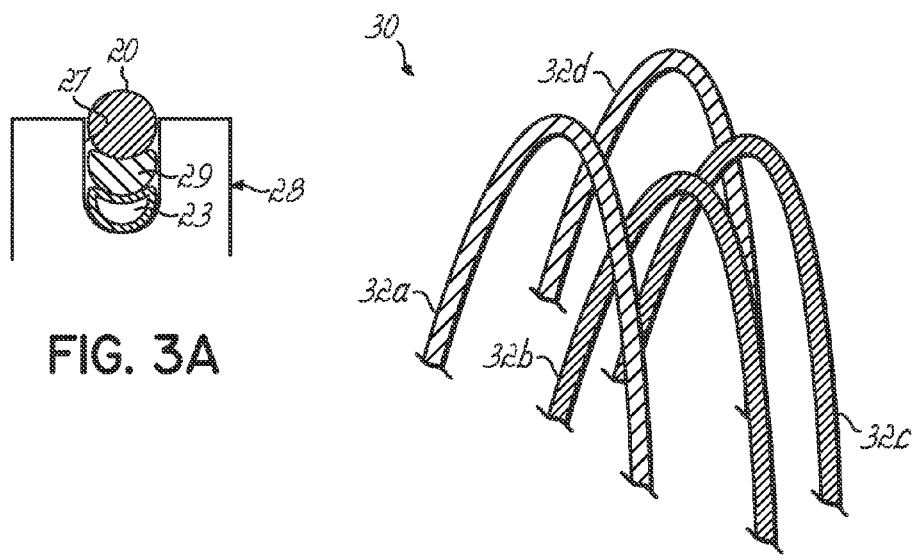
FIG. 3A
FIG. 4

MUSCLE ENERGY CONVERTER WITH SMOOTH CONTINUOUS TISSUE INTERFACE

CROSS REFERENCE TO RELATED APPLICATIONS

Benefit is claimed of the filing date of Oct. 18, 2005 of U.S. provisional patent application Ser. No. 60/727,650. Such application is expressly incorporated herein by reference as if fully set forth herein.

FIELD OF THE INVENTION

The present invention relates to apparatus for delivering energy from muscles to power devices such as heart-failure treatment devices, non-cardiac devices, or other power consuming devices.

BACKGROUND OF THE INVENTION

Present apparatus and methods for delivering power to active heart-failure treatment devices or non-cardiac devices with similar energy requirements may be problematic. For example, power conduits comprised of wires and tubes penetrating the skin may become infected. Similarly, trans-integumental transformers may present the risk of power-draining electromagnetic cross-coupling. Neither nuclear nor chemical batteries have proven to be effective for powering quantities beyond those of pacemakers and defibrillators. Likewise, power supply limitations and issues limit the practicality of various non-cardiac devices as well.

To address these limitations, the linear harnessing of contractile power from multiple in situ skeletal muscles has been investigated. Under this approach, underutilized, nonessential skeletal muscles are left in their natural sites, where they are conditioned to fatigue resistance and paced using techniques first developed in the cardiomyoplasty field. The tendon or distal muscle is connected to a hydraulic or other type of energy converter rather than to its natural insertion member, such as a bone.

Examples of specific muscles that have been harnessed in accordance with the principles described above include the psoas major, pectoralis major, latissimus dorsi, rectus abdominis, and one or more heads of the quadratus femoris muscles. These muscles have been shown to reliably and repetitively produce displacements in the range of about 10 to about 25 mm at mean contractile forces of about 10 to about 50 N, thereby yielding stroke work in the range of about 100 to about 1250 N-mm (equivalent to about 0.1 to about 1.25 Joules) per individual muscle. Ten percent of this energy may be recouped elastically and briefly stored for pre-stretch (pre-loading) to improve efficiency for subsequent beats. Assuming transmission efficiency losses of about 50% and rates in the range of about 25 to about 30 contractions per minute per muscle, harnessing of, for example, 2 to 6 muscles, may produce sufficient power for full circulatory power requirements (1 to 1.5 W). These values are averaged both over time and population. However, time-varying alterations and individual differences in energy potential may parallel similar differences in energy requirements. Thus, while circulatory power requirements may be greater during brief intervals of time (e.g., during heavy exercise), skeletal muscle potential may also be greater during the same time intervals. Similarly, both circulatory power requirements and nonessential skeletal muscle power potential may generally vary with body size and may be greater or lesser than the estimated average population values described above.

Linear harnessing of multiple in situ skeletal muscles, requires at least four technical capabilities. Linear harnessing may require, for example, approaches to effectively pace skeletal muscles for indefinite periods as well as methods to transform both muscle biochemistry and performance from anaerobic to aerobic, i.e., from quick bursts during exercise to the lower powered but non-fatiguing behavior most commonly seen in the flight muscles of birds. Similarly, linear harnessing of multiple in situ skeletal muscles may require methods of coupling muscles or their tendons to non-living (prosthetic) mechanical members capable of durable force transmission and methods of transferring the power so harvested to an active circulatory support device such as a total artificial heart, a ventricular assist device, a counterpulsator, or other like devices.

The required methods of coupling muscles or their tendons to non-living mechanical members capable of durable force transmission have been taught, for example, by U.S. Pat. Nos. 6,214,047 and 6,733,510 both issued to Melvin. The requirement of methods of transferring the power to an active circulatory support device, however, has not been demonstrated to be reliable over extended time periods notwithstanding, for example, the teachings of hydraulic systems in U.S. Pat. No. 5,888,186 to Trumble, U.S. Pat. No. 5,718,248 to Magovern and U.S. Pat. Nos. 5,984,857; 5,701,919; 5,653,676; and 5,344,385, all assigned to Thoratec, Inc.

The limitations of these devices taught in the prior art (referenced above) lie in the imposed movement of discrete parts through tissue required by their respective operations, which may result in an increased potential for scarring tissue which may tend to immobilize and limit motion. These devices are also limited by their physical bulk and by the potential of hydraulic seals to fail in their welded metal bellows or piston mechanisms.

SUMMARY OF THE INVENTION

A device for converting the contractile work of skeletal muscles into transportable energy may comprise a converter having a mobile end adapted to be connected to a skeletal muscle, a relatively stationary end opposite the mobile end; one or more energy processing units operatively connected to the mobile and stationary ends of the converter, with each energy processing unit adapted to convert tensile forces generated by contraction of the skeletal muscle into transportable energy, and one or more energy conduits such as electrical wires associated with the relatively stationary end of the converter for delivering the transportable energy to power-consuming devices implanted in a body. The device may further comprise a relatively stationary end that is operatively connected to a body structure that is stationary relative to the skeletal muscle. The device may be formed from a pair of tension elements in a steep serpentine pattern and include one or more energy processing units positioned between the tension elements, with such energy processing units having piezoelectric crystals adapted to convert contractile forces into electrical energy.

In another embodiment, a method of converting the contractile work of skeletal muscles into transportable energy may comprise connecting a mobile end of a converter to skeletal muscle, connecting a stationary end of the converter to a body structure that is stationary relative to the skeletal muscle, converting the contractile work of the skeletal muscle into transportable energy, and delivering the transportable energy to a power-consuming device implanted in a body.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 2B is a schematic view of an exemplary tension member used with the converter of FIG. 2.

FIG. 3 is a detailed view of an alternative embodiment of a muscle-energy converter at the point of contact between a tension member and an energy-processing unit.

FIG. 3A is a cross-sectional view of the embodiment of FIG. 3.

FIG. 4 is a perspective view of an alternative embodiment of a muscle-energy converter.

DETAILED DESCRIPTION

Figure 1:
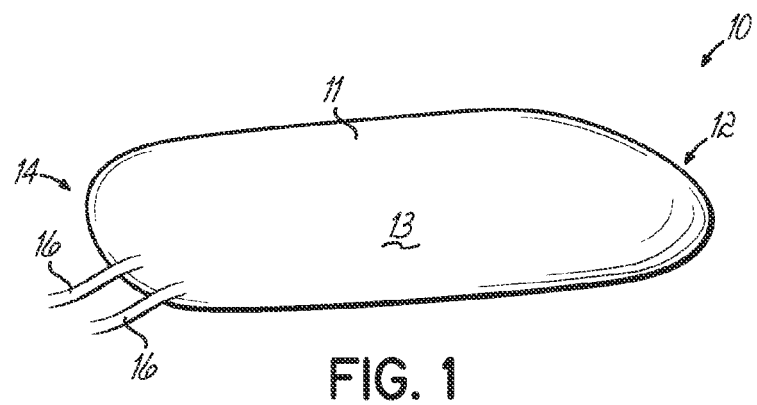
FIG. 1 is a perspective view of a muscle-energy converter.

With reference to FIG. 1, a converter 10 is an elongated structure generally having a length and width similar to those of the tendon of a muscle (not shown) to which they are applied and a thickness not exceeding an order of magnitude greater than the thickness of the native tendon. Converter 10 has a body 11 having a tissue-facing surface 13, a mobile end 12 and a longitudinally opposed relatively stationary end 14. One or more energy conduits 16 protrude from the relatively stationary end 14 to conduct energy from the converter 10 to a power-consuming device (not shown) such as a circulatory device utilizing the energy from the converter 10. Energy conduits 16 may comprise, for example, electrical wires, hydraulic tubes, mechanical conduits such as a cable-in-sheath, or any other suitable mechanism.

The mobile end 12 of the converter 10 is connected to a muscle at a point proximate the musculotendinous junction. Methods of connecting the converter 10 may for example include fiber-based tissue-interface devices such as those taught in U.S. Pat. No. 6,214,047, issued to Melvin, in conjunction with stress-distributing fiber termination devices such as those taught in U.S. Provisional Patent Application No. 60/642,016, the disclosures of which are incorporated by reference herein in their entirety. Alternatively other methods may be used, including or not including removal of the tendon. The relatively stationary end 14 of the converter 10 may be fixed either to a human or animal body structure that is stationary relative to the origin of the muscle to which the converter 10 is attached or it may be alternatively attached to other converters connected to one or more other muscles generating force in an opposite direction.

With continued reference to FIG. 1, converter 10 may be implanted in the body of a human or an animal. Converter 10 may convert contractile work (i.e. linear-displacement/tensile-force) of one or more skeletal muscles to a form of energy that is more readily transportable for circulatory assistance or other use. Energy may be converted, for example, into electrical energy, hydraulic energy, or lower-displacement/higher-force mechanical energy. Conversion may comprise transmitting the force and displacement of the muscles to inert mechanical parts such as a cable in a sheath suited for transmission. The embodiments herein described may facilitate useful harnessing of non-essential muscles which have been fitted with electrodes and pulse-generators for repetitive pacing and conditioned for sustained, aerobic, non-fatiguing performance.

The tissue-facing surface 13 of the body 11 of the converter 10 may be designed so that the motion of one part of that surface 13 relative to another (with possible exception of any mechanical—as opposed to hydraulic or electrical—converter-to-energy-conduit junctions) is effected solely by elastic or viscoelastic deformation. Converter 10 may further comprise indentations or fenestrations, in which case the surface 13 may be designed such that there will be no more than about a 50% reduction in any potential gap or space (and thus no more than about a 50% compressive strain delivered to any insinuating tissue) on the surface 13 throughout an active cycle.

With continued reference to FIG. 1, the interface between active elements of the converter 10 and surrounding tissue may be such that there is direct exposure of energy-converting components such as springs, tension elements, compressive elements, piezoelectric materials or electrical conduits, to tissue. These energy-converting components may comprise continuous or discontinuous coatings to provide electrical insulation, mechanical smoothness, biocompatibility, and/or other desirable features. These components may be configured not to encourage tissue ingrowth, thereby preventing immobilization.

Figure 1A:
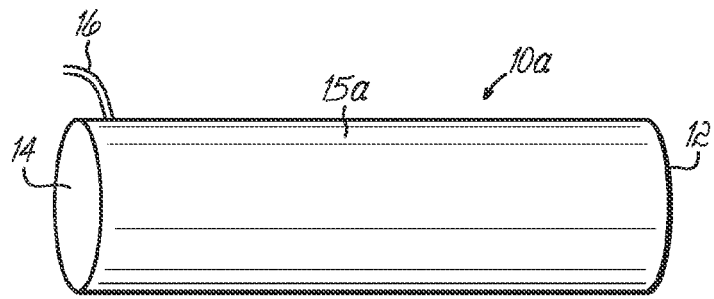
FIG. 1A is a perspective view of a muscle-energy converter having an encasing block.
Figure 1B:
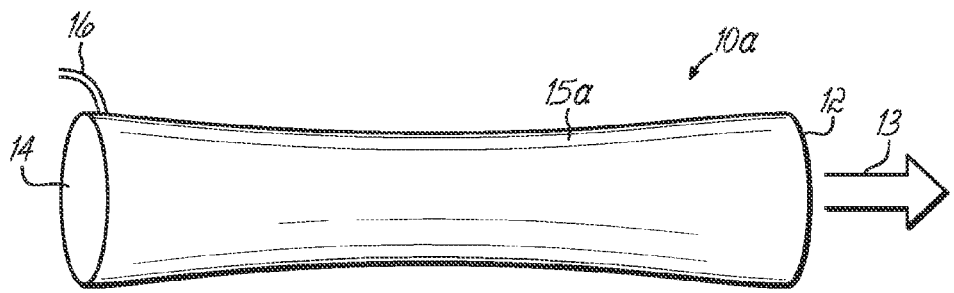
FIG. 1B is a perspective view of the converter of FIG. 1B in an extended condition.

With reference to FIGS. 1A-B, in which like reference numerals refer to like features in FIG. 1, a converter 10a, including energy conduit 16 may comprise an encasing block 15a as an interface between active elements of the converter 10a and surrounding tissue (not shown). Encasing block 15a may comprise a solid, low-modulus/strength ratio elastomer, such as low-durometer silicone rubber, having, for example, an ultimate failure strain of at least 250%, and further having a surface reinforced for toughness. The surface may be reinforced for toughness for example, by locally altering the chemical composition or by locally adding materials such as flocked fibers. With reference to FIG. 1B, encasing block 15a may stretch in accordance to a tensile force, depicted by arrow 13, applied by action of a muscle or the like to which converter 10a is connected. Encasing block 15a may be designed such that it does not stretch by more than about 25% of its original length during cyclic operation, or alternatively such that it does not exceed about $\leqq$10% of the failure strain of the elastomeric material defining encasing block 15a.

Figure 1C:
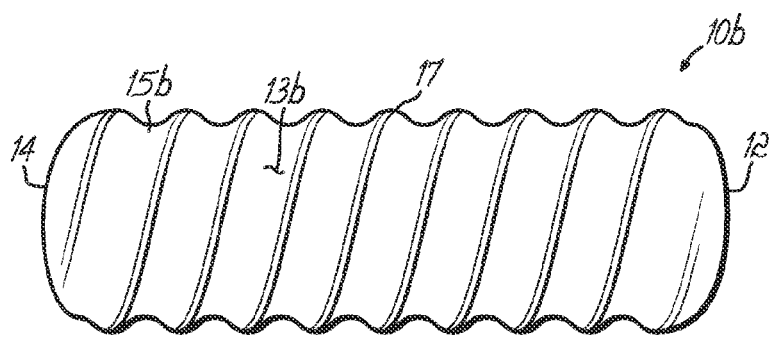
FIG. 1C is a perspective view of a muscle-energy converter having a corrugated encasing block.
Figure 1D:
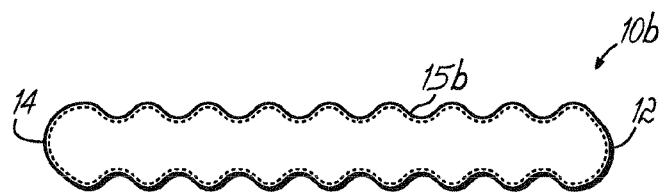
FIG. 1D is a perspective view of the converter of FIG. 1C in an extended condition.

With reference to FIGS. 1C-1D, in which like reference numerals refer to like features in FIG. 1, an exemplary converter 10b, having a surface 13b, a mobile end 12 and a relatively stationary end 14, may comprise an encasing block 15b, similar to encasing block 15a (FIGS. 1A-1B), including corrugations 17 on the surface 13b. The design of encasing block 15b may be such that the material strain of the surface 13b is sufficiently less than the global proportional block stretch and such that the global strain does not exceed $\leqq$10% of the failure strain of the material defining encasing block 15b.

Figure 1E:
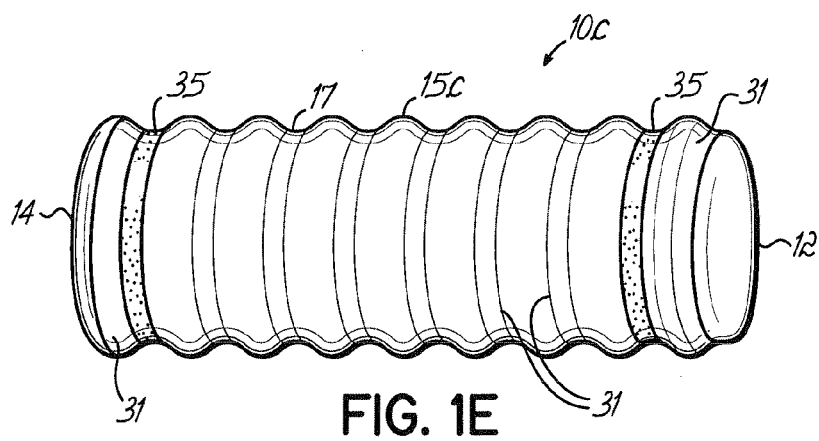
FIG. 1E is a perspective view of a muscle-energy converter having solid end blocks and an envelope containing a fluid.
Figure 1F:
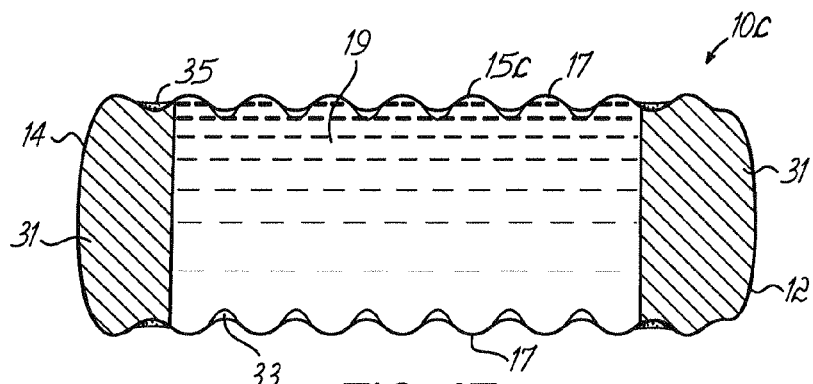
FIG. 1F is a cross-sectional view of the converter of FIG. 1E.

With reference to FIGS. 1E-1F, in which like reference numerals refer to like features in FIGS. 1 and 1C, an exemplary embodiment of a converter 10c may comprise an interface between active elements of the converter 10c and surrounding tissue (not shown) in the form of an envelope 15c having corrugations 17 and containing a fluid bath 19 such as a gel or oil. Envelope 15c may be made of an elastomeric material such as mold-cast silicone rubber, solution-cast polyurethane or any other suitable flexible material. Converter 10c may further comprise a mobile end 12 and a relatively stationary end 14. Mobile and relatively stationary ends 12, 14 may comprise solid blocks 31 made of suitable materials having moduli in a relatively wide range. Mobile and relatively stationary ends 12, 14 may, for example, comprise an elastomeric material, stainless steel or titanium and have respective constructions suitable for leak-free fixation to the envelope 15c. Fixation to envelope 15c may comprise binding, thermal welding, solvent sealing, adhesives, or other suitable components and/or methods.

An exemplary embodiment of a converter 10c may, for example, comprise cast polyurethane elastomer blocks 31 for the mobile and relatively stationary ends 12, 14. Such blocks may be internally reinforced by fiber inclusion distributed and oriented to facilitate firm fixation to the active energy converting components of the converter 10c, such as muscle coupling and solid tissue. An exemplary embodiment of converter 10c may further comprise a solution-cast polyurethane membrane envelope 15c having transverse corrugations 17 that may be solution-bonded to the blocks 31. This embodiment may also comprise internal contact bars 33 made, for example, of metal, polymer, or ceramic on the inner face of corrugations 17 to control friction against internal working members, and a reinforcing binding 35 at each block/envelope junction comprising, for example, a polyurethane-impregnated fine polyester fiber wrap.

Figure 1G:
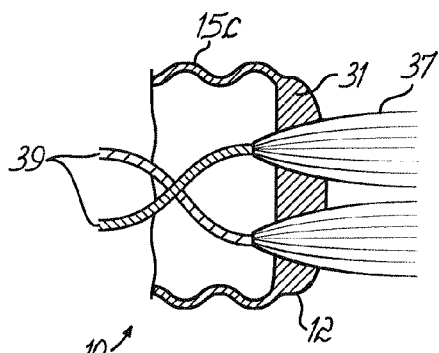
FIG. 1G is a partial schematic view of the mobile end of a muscle-energy converter having a fibrous connection to a muscle.

With reference to FIG. 1G, in which like reference numerals refer to like features in FIGS. 1, 1E and 1F, a converter 10 having a mobile end 12 may be affixed to a contracting skeletal muscle using any suitable method. For example, the method disclosed in U.S. Pat. No. 6,214,047, disclosing a muscle-coupling device, may be utilized. Such a coupling device may be fixed to the converter 10 taught herein by suitable methods such as welding, set-screw fixation or compression fixation. Alternatively, any other device may be utilized that converges to one or more compact cords and which may further comprise a compression plate of the type known to those familiar with the art of orthopedic surgery.

With continued reference to FIG. 1G, an exemplary method of fixation of a muscle to the mobile end 12 of a converter 10, having an encasing block 15c and a solid end block 31, may comprise fibers 37 that continue through the length of the converter 10 and are organized into cord-like tension elements 39 over such length. In this exemplary embodiment, the interface of the mobile end 12 of the converter 10 with the muscle comprises only the continuing fibers 37 and the encasing block 15c. Alternatively, a similar configuration is contemplated with a converter not having an encasing block 15c. In a converter that may incorporate an oil or gel-filled membrane to contain the active elements (as described above), the terminus of the converter at the mobile end 12 may also serve as a fixation point for that end of the tubular membrane, which may further be bound, adhered, or otherwise fixed to its surface circumferentially.

Figure 1H:
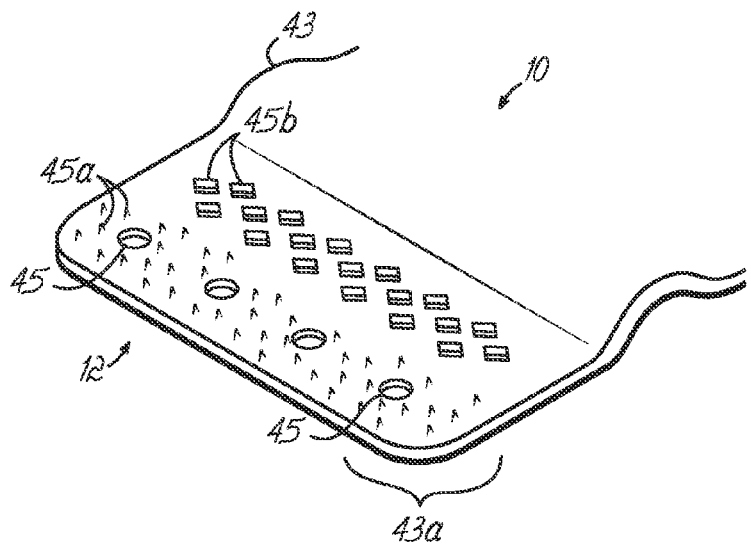
FIG. 1H is a partial view of the relatively stationary end of a muscle-energy converter.

With reference to FIG. 1H, in which like reference numerals refer to like features in FIG. 1, a converter 10 having a mobile end 12 and a relatively stationary end 14 (FIG. 1) may comprise a rigid or semi rigid fixating structure 43 that is securely fixed to the active, energy-converting elements (not shown) of converter 10 by any suitable methods such as those described above for fixation of the mobile end 12. The material and construction of the fixating structure 43 may be such that it provides a sufficiently strong interface for fixation of energy-converting elements to fixating structure 43 and for fixation of fixating structure 43 to a skeleton or another converter. Fixating structure 43 may, for example comprise a polymer, a ceramic, a metal, or a fiber-matrix composite and may further comprise a plate-like portion 43a of suitable shape, size, and curvature. The fixating structure 43 may have features generally familiar to those acquainted with the art of orthopedic and general surgery for fixation of prosthetic elements to bony structures, such as holes 45 adapted, for example, to receive screws, sutures, wires, polymer bands or cables therethrough that may penetrate or encircle bones. The fixating structure 43 may further comprise other features such as surface texturing 45a and/or a plurality of perforations 45b to facilitate fibrous tissue ingrowth.

The fixating structure 43 may alternatively facilitate coupling to one or more other converters 10. Such coupling may comprise suitable methods or components that provide a smooth profile and include biocompatible materials. Components to facilitate such coupling may, for example, include screws, rivets, or self-locking colletts. In converters comprising a fluid such as oil or gel encased in an envelope containing the active elements, fixation of the relatively stationary end 14 may be facilitated by a circumferential surface suitable for fixation by binding, adhesives, or other suitable alternatives.

Figure 2:
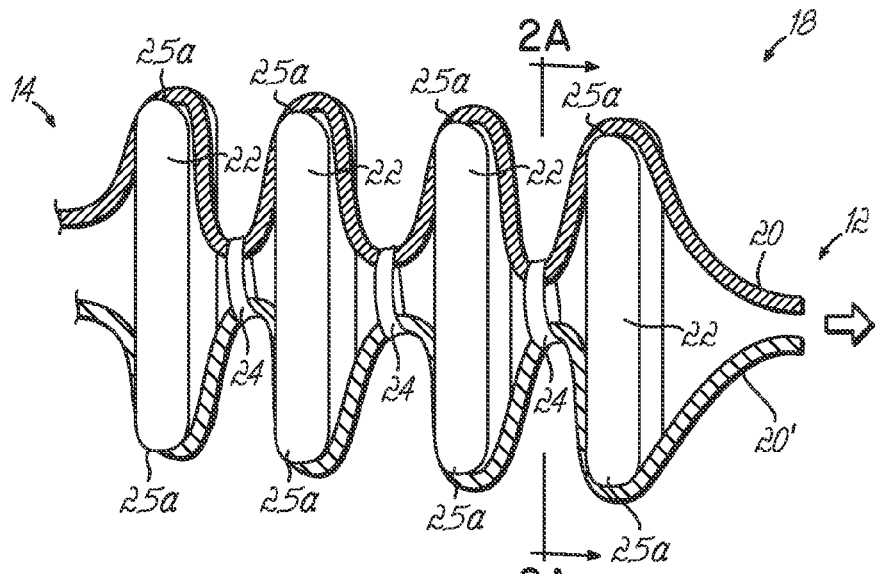
FIG. 2 is a perspective view of a muscle-energy converter having a set of steep serpentine springs.
Figure 2A:
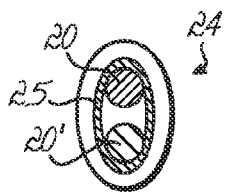
FIG. 2A is a cross-sectional view taken along line 2A-2A of FIG. 2.

With reference to FIGS. 2, 2A and 2B, in which like reference numerals refer to like features in FIG. 1, an exemplary converter 18 comprises a movable end 12, a relatively stationary end 14 and at least one pair of non-rigid tension elements 20, 20' in a steep serpentine pattern such as a sinusoidal pattern with wave-length/full-wave-amplitude ratio generally in the range of about 0.5 to about 1.0. Converter 18 may further comprise a corrugated elongated elastomeric envelope (not shown) filled with a liquid bath (not shown) comprising, for example, an oil or gel. Tension members 20, 20' may, for example, lie in the same plane and be 180 degrees out of phase with respect to each other. Converter 18 may further comprise energy processing units 22 and closed bands 24. The tension members 20, 20' may comprise flexurally stiff structures, such as stainless steel or titanium wires in the form of serpentine springs, or essentially flaccid elements such as cables. When tension members 20, 20' comprise flaccid elements, their shape may be maintained by the constraining effect of both the fixation members such as closed bands 24 and the energy processing units 22, both to be described below. Alternatively, other materials and structures defining tension members 20, 20' may be chosen to meet the requirements for strength, fatigue behavior, and elastic stiffness, both in flexion and elongation. A specific design of the tension elements 20, 20' may also be chosen to correspond to desired specific levels of strain energy to be stored in each cycle and the required amount of tensile preload for subsequent muscle actuation.

With reference to FIG. 2B, an exemplary embodiment of a tension member 20a comprises a high-durometer elastomeric rod 21a wrapped by a helical structure 21b made, for example, of stainless steel, titanium, or other biocompatible metal and then formed into a serpentine pattern in accordance with requirements of the particular converter being designed. Alternatively, the helical structure 21b may be preformed and injected with resin and a catalyst to polymerize the elastomeric rod in situ. Tension member 20a may further comprise a central high-strength fiber core 21c made, for example, of linearly crystalline polyethylene fibers such as Spectra®, in order to increase the longitudinal stiffness while maintaining flexural stiffness of tension member 21a. In another aspect of this embodiment, the construction of tension member 21a as described may be considerably less stiff to traction or to bending than a non-helical wire structure, and may advantageously present a broader contact surface for cyclic compression of the energy processing units 22.

With reference to FIGS. 2-2A, the tension members 20, 20' of this exemplary embodiment are securely held together at locations of proximity therebetween, such as locations corresponding to sinusoidal points at 90, 450, 810, 1170, and 1530 degrees for tension element 20 and corresponding sinusoidal points at 270, 630, 990, 1350 and 1710 degrees for tension element 20'. Securing of tension members 20, 20' may be exemplarily achieved by closed bands 24. Alternatively, securing of tension members 20, 20' may be achieved by any suitable method such as local binding, clasping, or through the application of other kinds of fixation members sufficiently strong to withstand projected forces potentially separating the tension members 20, 20' during cyclic activation of the converter 18, and having a high degree of durability to withstand potential friction-related wear arising from contact with the tension elements 20, 20'. With reference to FIG. 2A, each of the closed bands 24 is a generally elliptical member comprising an internal bearing surface 25. Closed bands 24 may be of a suitable material such as one similar to the material of which tension members 20, 20' are made and capable of securing, for example, tension elements 20, 20' made of stainless steel wire or titanium wire. The internal bearing surface 25 may comprise, for example, a hard polished ceramic or jewel-grade crystalline carbon such as industrial diamond.

With continued reference to FIG. 2, a plurality of schematically depicted generally elongated energy processing units 22 are disposed between the tension members 20, 20', for example, at points 25a, where tension members 20, 20' are farthest away from each other. The energy processing units 22 may comprise an assembly of embedded piezoelectric devices and mechanical stabilizing components. In operation, and due to their position with respect to tension members 20, 20', the energy processing units 22 are compressed when tension is applied on the tension members 20, 20'. Energy processing units 22 convert energy arising from their compression to a readily transferable form of energy. Each energy-processing unit 22 may comprise an assembly of piezoelectric elements (not shown) such as crystals, electrodes, insulating layers and coverings, and structural members to deliver the compressive force applied by the tension members as a distributed compressive force on the surface of piezoelectric elements. Energy-processing units 22 may further comprise mechanical members to stabilize the energy-processing units against columnar buckling in cases where their design carries a high aspect ratio. In this exemplary embodiment, the output of the energy-processing units 22 is in the form of electrical energy.

In operation, tensile force (i.e., traction) generated by muscle contraction is applied to the movable end 12 of the converter 18, thereby inducing elongation of the assembly that defines converter 18. The elongation of the tension members 20, 20' biases the points 25a inwardly. This motion of points 25a is of relatively low amplitude but produces a corresponding compressive force of relatively large magnitude against the ends of the energy-processing units 22, with an associated energy that is in turn converted by the piezoelectric elements into electrical energy. Electrical energy collected from each of the energy processing units 22 in the converter 10 may then be delivered by efferent transmission lines to the energy-consuming target device, via a circuit that may include energy storage and control components.

With reference to FIGS. 3-3A, in which like reference numerals refer to like features as in FIGS. 2-2A, an alternative embodiment of a converter 26 similar to converter 18 of FIGS. 2-2A comprises tension members 20,20' contacting hydraulic energy-processing units 28 at points 25a. Each hydraulic energy-processing unit may include a serpentine tube 23 and a compression plate 29. Each end of a hydraulic energy-processing unit 28 may comprise a groove 27 adapted to fully receive a serpentine tube 23, at least partially receive a tension member 20, 20', and fully receive a compression plate 29 therebetween. Hydraulic energy-processing units 28 may generally comprise a non-compressible block made, for example, of a ceramic material. Converter 26 may further comprise a corrugated elongated elastomeric envelope (not shown) filled with a liquid bath (not shown) comprising, for example, an oil or gel.

With continued reference to FIGS. 3-3A, application of longitudinal traction to the converter 26 results in relative inward motion of points 25a of tension members 20, 20', thereby applying a force in a direction into groove 27. This force is transmitted by compression plate 29 to the serpentine tube 23 which consequently deforms, thereby converting the compressive energy into hydraulic energy.

Figure 5:
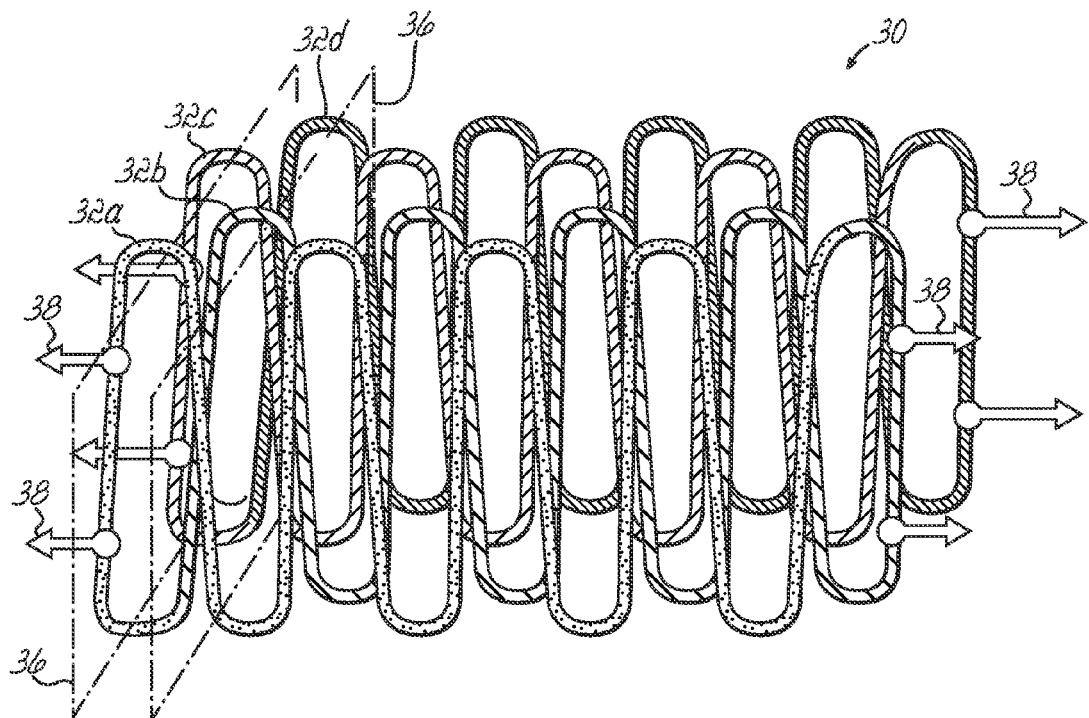
FIG. 5 is a perspective view of an alternative embodiment of a muscle-energy converter similar to the embodiment of FIG. 4.

With reference to FIGS. 4-5, in which like reference numerals refer to like features in FIG. 2, an alternative embodiment of a converter 30 is similar to converter 18 (FIG. 2) but it includes a different arrangement of tension members such as tension members 32a, b, c, d of FIG. 4. Each pair of tension members 32a, b, c, d comprises 180-degree out-of-phase serpentine tension members lying in adjacent parallel planes, such that the paths of the two tension members 32a, b, or 32c, d in any given pair cross at each half-wave length point. For purposes of illustration, in the exemplary embodiment of FIG. 4, the path of tension member 32a begins at the central axis of the converter 30 at 0 degrees, while tension member 32b follows a path that begins at the central axis at 180 degrees. Tension members 32a, b may cross again at points respectively corresponding to 180 degrees for the tension member 32a and 360 degrees for tension member 32b, at 360 degrees for the tension member 32a and 540 degrees for the tension member 32b and at 540 degrees for the tension member 32a and 720 degrees for the tension member 32b.

In this exemplary embodiment, the energy processing units 22 (FIG. 2) are disposed such that they are compressed by the two tension members 32a, b in a pair at points every 180 degrees of the respective paths of tension elements 32a, b. For example, energy processing units 22 may be disposed at points corresponding to the 90 degree point of the tension member 32a and the 270 degree point of tension member 32b, the 270 degree point of the tension member 32a and the 450 degree point of tension member 32b, and so on. The energy processing units 22 may be identical to those described in the embodiment of FIG. 2 and their operation may follow the same principles as those in the embodiment of FIG. 2. Converter 30 may further comprise a corrugated elongated elastomeric envelope (not shown) filled with a liquid bath (not shown) comprising, for example, an oil or gel.

With reference to FIG. 5, an exemplary embodiment in accordance with the principles of the embodiment of FIG. 4 includes a symmetric phasic pattern of tension members 32a, b, c, d that may be used when converter 30 comprises more than one pair of tension members. The arrangement of tension members 32a, b, c, d of FIGS. 4-5 may lessen the tendency of converter 30 to torque, due to the symmetry of forces (symbolized by arrows 38) applied to the tension members 32a, b, c, d arranged as shown in FIGS. 4-5. Progressing from one end of the converter 30 to the other, paths of tension members would be in parallel planes 36 in a symmetrical pattern from one end to the other.

While the converter 30 in the embodiments of FIGS. 4-5 has been described as comprising energy-processing units 22 having piezoelectric elements, persons of ordinary skill in the art will appreciate that, alternatively, converter 30 may comprise hydraulic energy-processing units such as the energy processing units 28 in the embodiment of FIGS. 3-3A. Converter 30 may further comprise a corrugated elongated elastomeric envelope (not shown) filled with a liquid bath (not shown) comprising, for example, an oil or gel.

Figure 6:
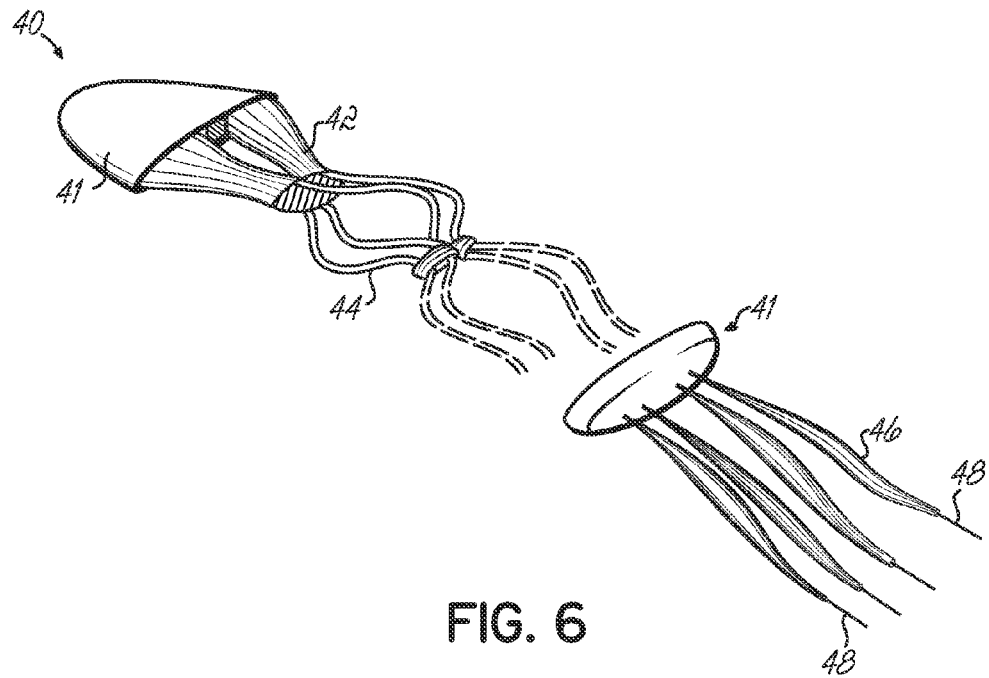
FIG. 6 is a perspective view of an alternative embodiment of a muscle-energy converter including a muscle-coupling device.

With reference to FIG. 6, converters 18, 20, 26, 30 (FIGS. 2-5) may be alternatively constructed as depicted, having a wafer-type muscle-coupling device 40 affixed to the converter. Muscle-coupling device 40 may comprise an enveloping assembly 41 and a plurality of fine fibers 42 projecting therefrom and made, for example, of polymer, metal, or other suitable material, as described in U.S. Provisional Patent Application No. 60/642,016. Envelope assembly 41 may be rigid or semi-rigid and may be made, for example, of a biocompatible metal such as titanium or a biocompatible fiber-matrix composite such as carbon-fiber epoxy, suitable for hard tissue fixation. When muscle-coupling device 40 is used, and as taught, for example, in U.S. Pat. No. 6,214,047, fibers 42 exiting the muscle-coupling device extend without interruption or inter-material junctions through the converter. Fibers 42 are then divided into the one or more pairs of tension members 44, and are configured and arranged to operate in the same way as described above for the tension members in the embodiments of FIGS. 2-5. The relative arrangement of tension members may also follow the arrangement of tension members described in the embodiments of FIGS. 2-5. An advantage of using muscle-coupling device 40, as described above, lies in the potential reduced probability of having an inter-material load-bearing junction at the mobile end 12 of the converter, which may reduce the potential for stress concentration, thereby mitigating fatigue failure risk.

With continued reference to FIG. 6, the fibers 42 extend from the muscle-coupling device 40 into the converter. Within the converter, fibers may be organized into an even number of parallel bundles or tows, and each bundle may be impregnated with an elastomeric material and wound with a titanium or stainless steel spring-tempered helix to define tension members 44. Fibers 42 may exit the converter free of the elastomeric material, and be regrouped into bundles 46 of suitable size for passage into a muscle, and may further be fitted with needles 48 or the like adapted for muscle insertion as taught in U.S. Pat. No. 6,214,047.

Figure 7:
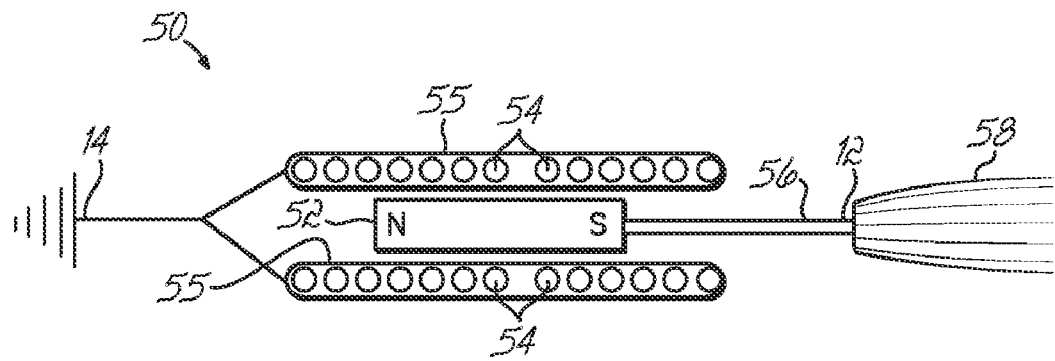
FIG. 7 is an elevation view of an alternative embodiment of a muscle-energy converter.
Figure 7A:
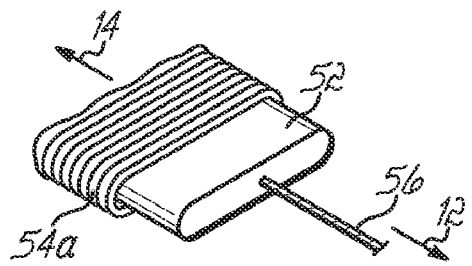
FIG. 7A is a partial perspective view of the embodiment of FIG. 7.

With reference to FIGS. 7-7A, in which like reference numerals refer to like features in FIG. 1, an alternative embodiment of a converter 50 with linear magneto-electrical induction comprises a mobile end 12, a relatively stationary end 14, one or more energy conduits 16 (not shown), a connecting cord or cable 56 and one or more intermittently moving electric magnets 52 surrounded by field coils of electrical conductors 54. Converter 50 may be connected to a cyclically contracting muscle 58 proximate the movable end 12. The field coils 54 may be surrounded by insulating layers 55, and may be affixed to the relatively stationary end 14 of the converter 50, thereby restricting its movement along a major dimension of the converter 50. Persons of ordinary skill in the art will appreciate that field coils 54 may take on one or more of several specific mechanical arrangements of coil position, coil numbers, winding density, combinations of parallel and series connections, and core material if any (such as high-permeability material). Such arrangements may further be optimized by computer modeling of electromagnetic fields. Converter 50 may further comprise a corrugated elongated elastomeric envelope (not shown) filled with a liquid bath (not shown) comprising, for example, an oil or gel.

With reference to FIG. 7A, an exemplary embodiment of the converter 50 may comprise field coils in the form of a flattened elliptical or 'race-track shape' helical winding of insulated electrical conductors 54a proximate the relatively stationary end 14 of the converter 50.

In this exemplary embodiment, and with reference to FIGS. 7-7A, the field coils 54 and 54a may comprise insulating layers 55. Converter 50 may further comprise a magnet insulator (not shown). Permanent magnet 52 may slide along with the insulating layers 55 of the field coils 54, therefore presenting requirements for the materials that define insulating layers 55 and the magnet insulator. Materials for the insulating layers 55 and the magnet insulator may, for example, be chosen based on demonstrated long-term and high-cycle durability under similar loads and lubrication. For example, the permanent magnet 52 may comprise a polished titanium jacket while the insulating layers 55 of the field coils 54 may comprise an ultra-high molecular weight polyurethane lining.

With continued reference to FIGS. 7-7A, a flexible cord or cable 56 affixes the magnet 52 to the mobile end of the converter 50. Because of potential for either fixed curvature and/or occasional bending of the available anatomic space (e.g., over the rib cage with breathing and coughing), the cable 56 may pass through spacers (not shown) within corrugations from the magnet 52 to the mobile end 12 of the converter 50. Materials for the cable and spacers may be chosen based on demonstrated long-term and high-cycle durability under similar loads and lubrication. For example, the cable 56 may comprise titanium or stainless steel while the spacers may comprise machined ultra-high molecular weight polyurethane blocks. The arrangement herein described may allow shortening to occur over the entire length of a membranous corrugated envelope (if present), distributing strain over the entire corrugated length, while the magnet/coil displacement is located only at one end of that space. Only the magnet/coil segment of the space may need to be rigid or non-bending.

Figure 8:
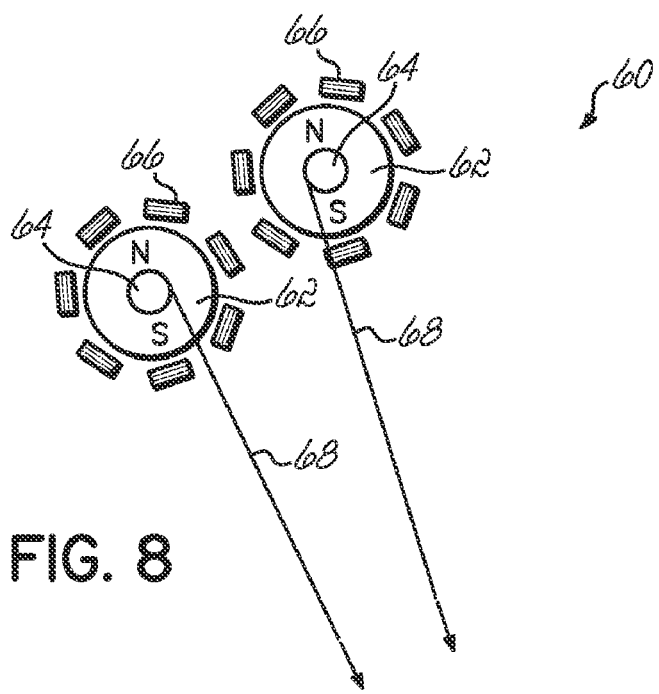
FIG. 8 is a partial schematic view of an alternative embodiment of a muscle-energy converter.

With reference to FIG. 8, an alternative embodiment of a converter 60 with rotary magneto-electrical induction comprises two oppositely-turning rotary magnets 62 coupled to respective cables or tethers 68 via respective pulleys 64 affixed proximate the respective centers of each magnet 62. Electrical field coils 66 at least partially surround the rotary magnets 62 or may alternatively be arranged in any suitable manner consistent with conventional patterns known to those in the art of power electrical engineering. Coil numbers, winding density, combinations of parallel and series connections and other features of converter 60 may be further optimized by computer modeling of electromagnetic fields. Converter 60 may further comprise a corrugated elongated elastomeric envelope (not shown) filled with a liquid bath (not shown) comprising, for example, an oil or gel.

While the embodiment in FIG. 8 depicts respective cables 68 on one side of each magnet 62, persons of ordinary skill in the art will appreciate that, alternatively, converter 60 may comprise two sets of cables 68 and two corresponding sets of pulleys 64, such that each side of each magnet comprises a pulley 64 and a cable 68 wound about it. This may be desirable, for example, to minimize any observed bending moments induced by the motion of the cables 68. Material considerations for choice of materials defining the cables 68 and pulleys 64 are similar to those described for the embodiment of FIGS. 7-7A.

Figure 9:
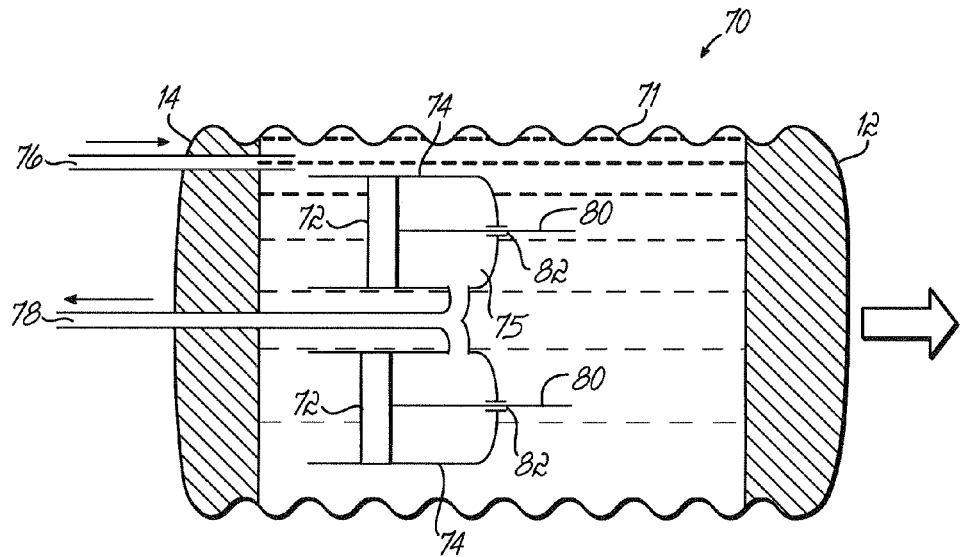
FIG. 9 is a cross-sectional view of an alternative embodiment of a muscle-energy converter.

With reference to FIG. 9, in which like reference numerals refer to like features in FIG. 1, an alternative embodiment of a converter 70, that may include a corrugated elongated elastomeric envelope 71 filled with a liquid bath comprising, for example, an oil or gel, may further include a mobile end 12, a relatively stationary end 14, and one or more hydraulic rigid cylinders 74 that use the same fluid as that which fills the interior portions of the converter 70 and which surrounds the cylinders 74. Converter 70 may exemplarily comprise two hydraulic cylinders 74 sharing an interior cavity 75 and affixed to the relatively stationary end 14 of the converter 70, energy conduits 76, 78 and rigid pistons 72 closely fitting within the cylinders 74. The pistons 72 may comprise piston rods 80 that extend through openings 82 at the base of the cylinders 74.

A first energy conduit 76 fluidly communicates the interior cavity 75 with the relatively stationary end 14 of the converter 70 and may comprise one or more flexible, very low compliance tubes adapted to transmit relatively high pressures, such as pressures in the range of several atmospheres. A second energy conduit 78 fluidly communicates the relatively stationary end 14 with the interior portion of the converter 70 surrounding the cylinders 74.

The converter 70 of this embodiment may not require piston rings or seals. Advantageously, the common fluid used by the cylinders 74 and surrounding the interior portion of the converter 70 may provide for the tolerance for and recycling of relatively small, controlled leaks within converter 70. A potential loss of transmitted energy due to leakage around a piston 72 and around piston rod 80, may be proportional to the leak. This leak may, in practice, be limited to a very small percentage, such as less than about 1%, of the fluid displaced by the cylinder 74. The wear-related benefits of having no seals or piston rings may constitute a trade-off for this potential energy loss.

Figure 10:
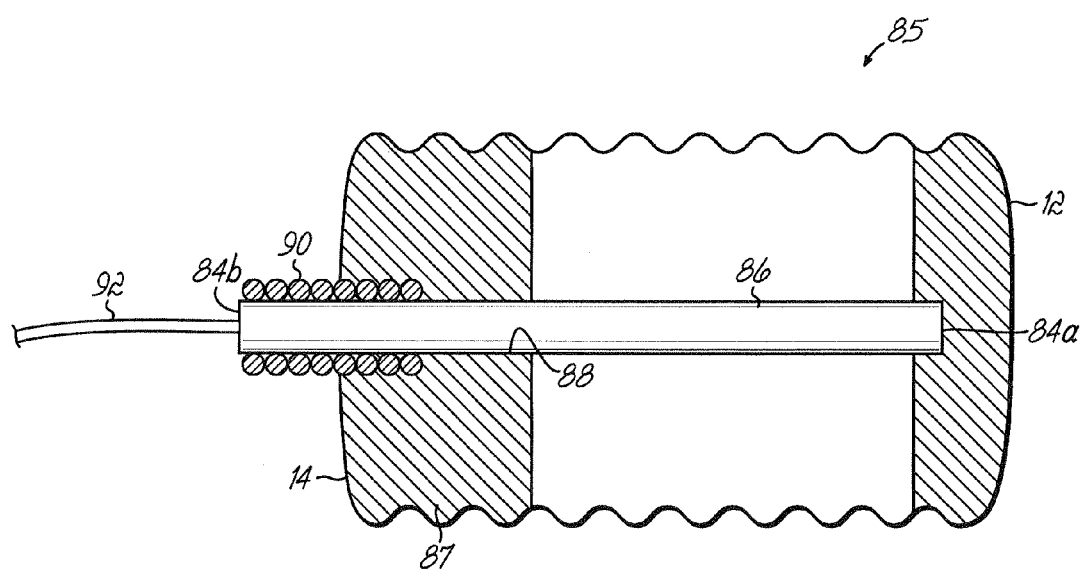
FIG. 10 is a cross-sectional view of an alternative embodiment of a muscle-energy converter.

With reference to FIG. 10, in which like reference numerals refer to like features in FIG. 1, an alternative embodiment of a converter 85 having direct linear mechanical transfer of energy, may comprise a mobile end 12, a relatively stationary end 14 in the form of a rigid block 87 and one or more energy conduits in the form of cables 92. Converter 85 may further comprise a rod 86 having first and second ends 84a, 84b and slidable within a bore 88 within the rigid block 87. The first end 84a of rod 86 is connected via one or more tethers (not shown) of suitable material and construction to the mobile end 12 of converter 85, while the second end 84b of rod 86 may be connected to energy conduits in the form of cables 92. A rigid compression sheath 90 comprising, for example, a helical coil or any other suitable configuration, may surround the rod 86 and the cables 92. In operation, muscular contraction induces uniaxial motion of the rod 86, thereby transferring energy therefrom to a power-consuming device (not shown) via cables 92.

While the embodiment of FIG. 10 depicts a converter 85 having a single rod 86 connected to a power-consuming device (not shown), persons skilled in the art will appreciate that converter 85 may alternatively comprise more than one rod 86 and/or more than one cable 92.

Figure 11:
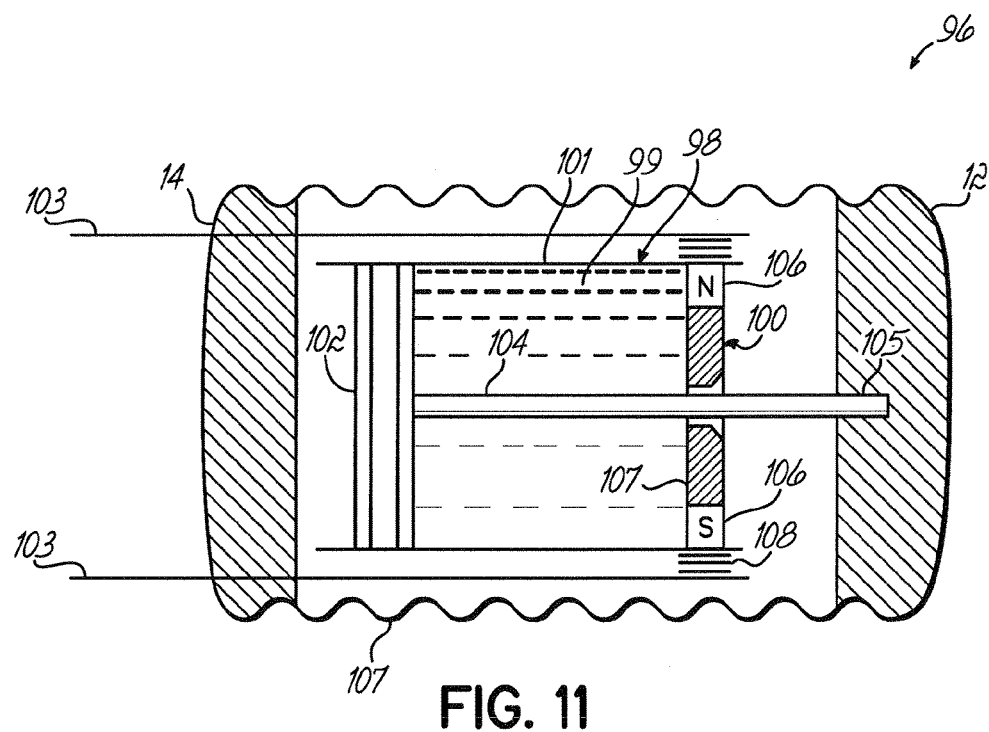
FIG. 11 a cross-sectional view of an alternative embodiment of a muscle-energy converter
Figure 11A:
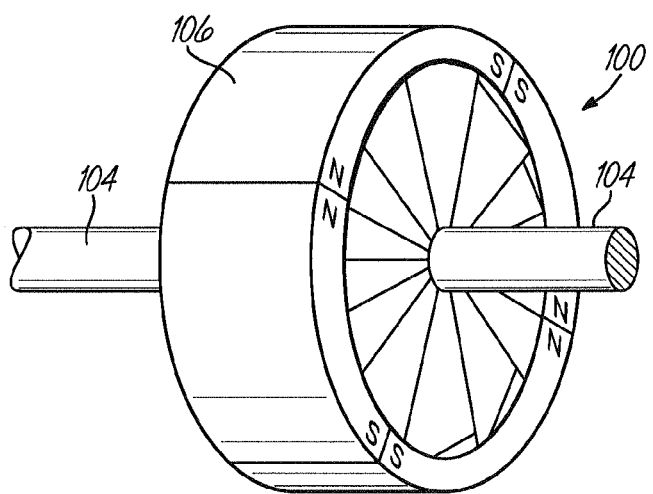
FIG. 11A is a partial perspective view of the embodiment of FIG. 11.

With reference to FIGS. 11-11A, in which like reference numerals refer to like features in FIG. 1, an alternative converter 96 that may include a corrugated elongated elastomeric envelope 107 filled with a liquid bath (not shown) comprising, for example, an oil or gel, may further comprise a mobile end 12, a relatively stationary end 14, and a piston 102 moving within a cavity 99 of a hydraulic cylinder 98. The piston 102 may include a piston rod 104 having an end 105 that may be affixed to the mobile end 12 of the converter 96. The cylinder 98 may be affixed to the relatively stationary end 14 of converter 96. A turbine 100 may be affixed to the cylinder and lie concentrically with the piston 102 such that the turbine 100 surrounds the piston rod 104 proximate the base 107 of the cylinder 98. Permanent magnets 106 may be coupled to the circumferential surfaces of the turbine 100 and indirectly (through a wall 101 defining cylinder 98) face a plurality of field magnets 108 in a suitable configuration such as a ring configuration affixed to the outer surface of cylinder 98. Wall 101 may be made of a non-magnetic material such as a polymer composite, a non-magnetic metal or any suitable material to permit interaction between permanent magnets 106 and field magnets 108. Electrical energy conduits 103 may be operatively connected to field magnets 108 and generally extend through the relatively stationary end 14 to communicate the converter 96 with a power-consuming device (not shown).

With continued reference to FIGS. 11-11A, contraction of a muscle connected to the mobile end 12 of converter 96 may cause relative sliding motion between the piston 102 and the cylinder 98, such that fluid filling the cavity 99 is expelled from the cylinder through turbine 100, thereby causing rotation of the turbine 100. Rotation of the turbine 100 may cause rotation of the permanent magnets 106 coupled to the circumferential surfaces of the turbine 100, which interact with field magnets 108 to induce electrical energy to flow from field magnets 108 through energy conduits 103.

With reference to FIGS. 12, 12A-C, an alternative embodiment of a converter 110 may comprise a mobile end 12, a relatively stationary end 14 and a plurality of serially connected hydraulic tubes 112 therebetween, each having first and second ends 113, 117. The mobile end 12 may be connected to a contracting, paced skeletal muscle while the relatively stationary end 14 may be connected to a skeletally fixed anchor or to an opposing muscle connection. Each hydraulic tube 112 may comprise an elastomer that may further be corrugated. The walls 115 defining hydraulic tubes 112 may comprise a plurality of relatively nonexpansile longitudinally oriented fibers 114 and relatively nonexpansile circumferentially oriented fibers 116. Fibers 114, 116 may be made of any suitable material having suitable tensile modulus, strength, and fatigue risk, such as steel or titanium. The longitudinally oriented fibers 114 may be predominantly located along an inner curvature portion 111 of each hydraulic tube while the circumferentially oriented fibers 116 may be predominantly located along the outer curvature portion 119 of the wall 115. This configuration may allow the inner curvature portion 111 to be relatively non-extendable with respect to the outer curvature portion 119 of the wall 115.

Figure 12:
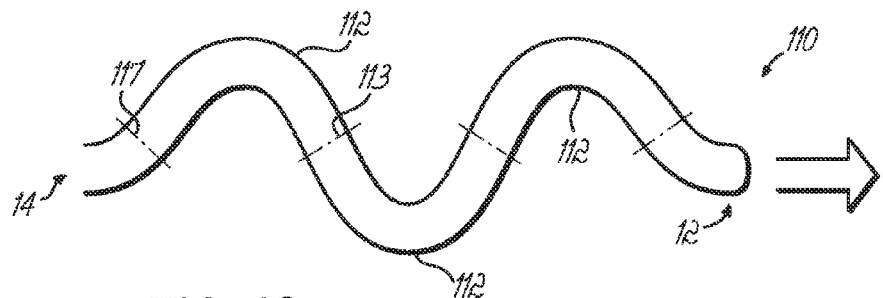
FIG. 12 is a partial elevation view of an alternative embodiment of a muscle-energy converter having tube sections.
Figure 12A:
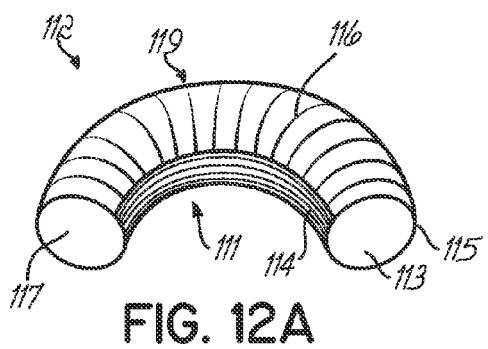
FIG. 12A is a partial perspective view of a tube section of the embodiment of FIG. 12.
Figure 12B:
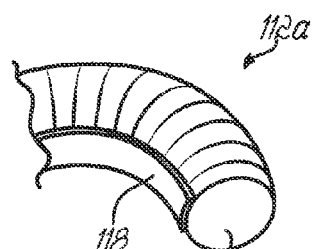
FIG. 12B is a partial perspective view of an alternative embodiment of a tube section of the embodiment of FIG. 12.

With reference to FIG. 12B, another embodiment of a hydraulic tube 112a similar to and following the same principles as the embodiment of FIGS. 12-12A replaces the plurality of longitudinally oriented fibers 114 of hydraulic tubes 112 with respective flexible bands or ribbons 118. Ribbons 118 may comprise a suitable construction and materials taking into consideration, for example, the maximum expected bending stress, reasonable engineering safety factors, risk of fatigue and the failure limit of the material defining the ribbons 118. Alternatively, tubes 112 may take the form of modified and bent elongated metal bellows (not shown), having the inner curvature portion 111 restricted by suitable methods or components.

Figure 12C:
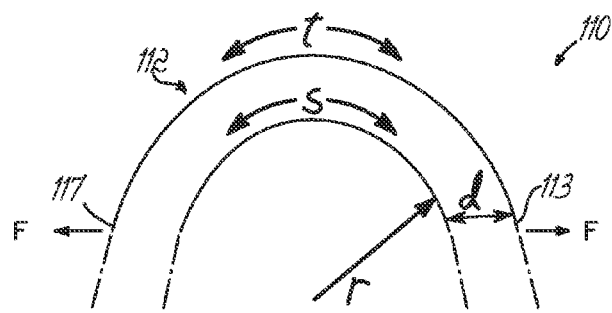
FIG. 12C is a schematic view of a tube section of the embodiment of FIG. 12.

With reference to FIGS. 12, 12A-B, in operation, when tension is applied between the ends 113, 117 of each hydraulic tube 112, the inner curvature portion 111 may straighten, thereby causing compression of the outer curvature portion 119 of the tube 112. With reference to FIG. 12C, the diameter of the tube 112 is labeled "d," the length of the inner curvature portion 111 of tube 112 is labeled "s," the length of a diametrically opposed line in the outer curvature portion 119 is labeled "t," and the radius of curvature is labeled "r." Upon the application of tension indicated by "F," the volume "V" of fluid held by tube 112 may decrease, as predicted by $[V=\pi \ast (r)2\ast (s+t)/2]$, since such tension increases the radius "r" of tube 112 and decreases the length "t" on the outer curvature portion 119 while the diameter "d" and the length "s" of the inner curvature portion 111 are both held constant.

With continued reference to FIGS. 12, 12A-C, in operation, the decrement in the volume of fluid held in tube 112 resulting from the application of tension on the ends 113, 117 may be harnessed, via hydraulic tubing (not shown) to regional or central hydraulic processing units where volume, pressure and timing adjustments may be delivered to render power to implanted devices or the like.

Figure 13:
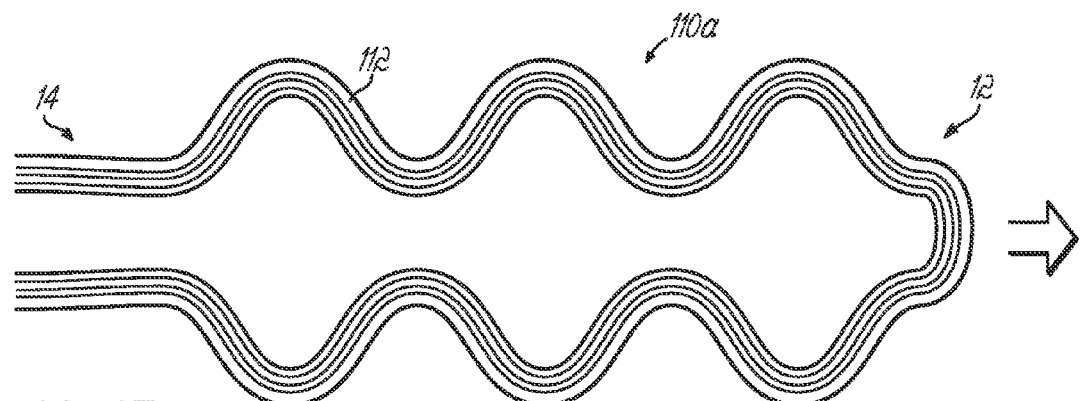
FIG. 13 is an elevation view of an alternative embodiment of a muscle-energy converter including tube sections.

With reference to FIG. 13, in which like reference numerals refer to like features in FIG. 12, an alternative embodiment of a converter 110a is very similar to converter 110 of FIG. 12 and likewise comprises a mobile end 12 and a relatively stationary end 14. Converter 110a similarly comprises hydraulic tubes 112 with similar functionality and characteristics as those described in the embodiment of FIGS. 12, 12A-C, and a description of which may be referred for an understanding of tubes in this embodiment as well. Tubes 112 in FIG. 13 are exemplarily arranged as depicted, such that serially connected segments of tubes 112 are parallelly and adjacently positioned. In operation, the same pressure that can be generated by one tube 112 may be delivered with a fluid volume that is the sum of the output of all tubes 112 in the converter 110a.

While the embodiments of FIGS. 12 and 13 are depicted as comprising serially connected segments of tubes 112 respectively comprising 3 or 5 tubes 112, persons of ordinary skill in the art will appreciate that any other number of tubes 112 may be alternatively serially connected. Likewise, while the embodiments depicted in FIGS. 12 and 13 are depicted as respectively comprising a single segment and 4 rows of parallelly positioned segments of tubes 112, persons of ordinary skill in the art will appreciate that any other number of segments of tubes 112 may be alternatively parallelly connected. The tubes 112 may comprise materials and geometric constructions such that the materials do not generally reach strains of more than about 30% of the materials' failure strain values.

Figure 14:
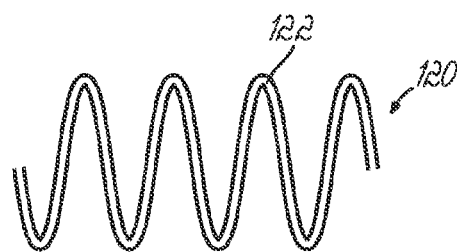
FIG. 14 is a partial elevation view of a tension spring.
Figure 14A:
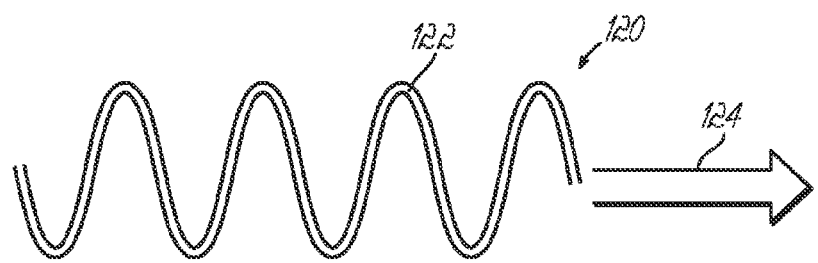
FIG. 14A is a partial elevation view of the tension spring of FIG. 14 in an extended condition.

With reference to FIGS. 14-14A, an exemplary serpentine spring 120, formed from a suitable wire 122, may extend parallelly with the tension members of a converter such as the converters 18, 26, 30, 40 (FIGS. 2, 3, 4, 6). The spring 120 is shown in both a compressed condition (FIG. 14) and an extended condition (FIG. 14A) resulting from action of an applied tensile force depicted by arrow 124. The spring constant and length of spring 120 may be chosen in accordance with the particular muscle being harnessed. The strain energy stored in the spring from compression of the converter, as described above, may affect the available amount of preload of the converter carrying spring 120. Preload is the state of elongation of a muscle secondary to applied tension before a contraction, whether such contraction results from spontaneous nerve impulse or from electrical pacing to a nerve or the muscle.

While spring 120 is depicted as a conventional tension spring, persons skilled in the art will appreciate that any other suitable configuration may be used, such those comprising a helical tension spring, a helical compression spring, a torsion spring or a corrugated band.

Figure 15:
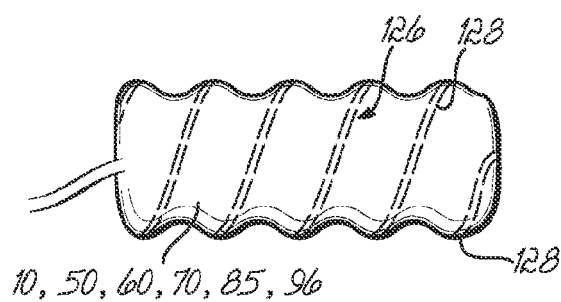
FIG. 15 is an elevation view of a helical spring and muscle-energy converter.
Figure 15A:
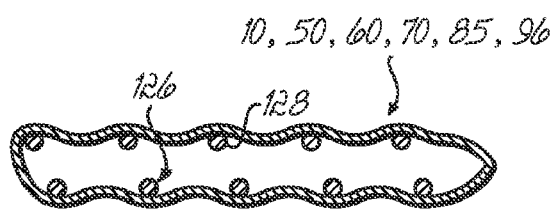
FIG. 15A is a cross-sectional view of the helical spring and muscle-energy converter of FIG. 15 in an extended condition.

With reference to FIGS. 15-15A, an exemplary helical tension spring 126, formed from a suitable wire 128, may partially define a converter such as converters 10, 50, 60, 70, 85, 96 (FIGS. 1, 7-11), all of which may have respective patterns of corrugations on their respective outer surfaces. Considerations for choice of material and design for the helical tension spring are the same as those described above for spring 120 (FIGS. 14-14A). The technical effect of spring 126 on a converter carrying it is also similar to that described above for spring 120.

Accordingly, many further embodiments, applications and modifications of the invention will become readily apparent to those of ordinary skill in the art without departing from the scope of the invention and applicant intends to be bound only by the claims appended hereto.

What is claimed is:

1. A converter for converting contractile work of skeletal muscles into transportable energy, comprising:
    a relatively stationary end and a mobile end opposite the relatively stationary end and adapted to be connected to a skeletal muscle for movement of the mobile end relative to the relatively stationary end;
    at least one pair of tension elements operatively positioned between the mobile and stationary ends of the converter, the tension elements arranged in a serpentine pattern defining pairs of points of a first distance between the tension elements, and pairs of points of a second distance between the tension elements, the first distance being greater than the second distance;
    at least one piezoelectric crystal disposed between the tension elements, the at least one piezoelectric crystal adapted to convert the relative movement of the mobile end into transportable energy; and
    at least one energy conduit associated with the relatively stationary end for delivering the transportable energy to a power-consuming device implanted in a body.

2. The converter of claim 1, wherein the relatively stationary end of the converter is adapted to be operatively connected to a body structure.

3. The converter of claim 1, wherein the relatively stationary end is operatively connected to a second muscle for movement of the relatively stationary end in a direction opposite to the relative movement of the mobile end.

4. The converter of claim 1, wherein the at least one energy conduit includes at least one of an electrical wire or a tube.

5. The converter of claim 1, wherein the at least one piezoelectric crystal is disposed between a pair of points of the first distance between the tension elements, wherein movement of the mobile end relative to the relatively stationary end is adapted to cause compression of the at least one piezoelectric crystal.

6. The converter of claim 1, further comprising at least one closed band coupled about a pair of points of the second distance between the tension elements, the closed band restricting the tension elements from movement relative to one another.

7. The converter of claim 1, wherein the mobile end includes fibers adapted for coupling to the skeletal muscle.

8. The converter of claim 1, further comprising an encasing block surrounding the tension elements.

9. The converter of claim 8, further comprising a fluid disposed within the encasing block.

10. The converter of claim 1, further comprising:
    a plurality of tension elements arranged in respective serpentine patterns, the plurality of tension elements arranged so as to minimize torsion of the converter upon the relative movement of the mobile end.

* * * * *